United States Patent [19]

Maier et al.

[11] Patent Number: 4,820,335
[45] Date of Patent: Apr. 11, 1989

[54] 1-SUBSTITUTED IMIDAZOLE-5-CARBOXYLIC ACID DERIVATIVES, THEIR PREPARATION AND THEIR USE AS BIOCIDES

[75] Inventors: Thomas Maier, Frankfurt am Main; Roland Schmierer, Gersthofen; Klaus Bauer, Rodgau; Hermann Bieringer, Eppstein/Taunus; Helmut Bürstell, Frankfurt am Main; Burkhard Sachse, Kelkheim, all of Fed. Rep. of Germany

[73] Assignee: Hoechst AG, Frankfurt am Main, Fed. Rep. of Germany

[21] Appl. No.: 867,813

[22] Filed: May 27, 1986

Related U.S. Application Data

[63] Continuation of Ser. No. 547,937, Nov. 2, 1983, abandoned.

[51] Int. Cl.⁴ .................. A01N 43/50; C07D 211/70
[52] U.S. Cl. .............................. 71/92; 514/400; 548/343
[58] Field of Search ............... 548/343; 71/92; 514/400, 399

[56] References Cited

U.S. PATENT DOCUMENTS

| | | | |
|---|---|---|---|
| 4,046,911 | 9/1977 | Hubele | 424/285 |
| 4,182,624 | 1/1980 | Söder et al. | 71/92 |
| 4,292,431 | 9/1981 | Kim et al. | 548/343 |
| 4,401,821 | 8/1983 | Plath et al. | 71/92 |
| 4,420,324 | 12/1983 | Eicken et al. | 71/92 |
| 4,637,828 | 1/1987 | Schülze et al. | 71/92 |

FOREIGN PATENT DOCUMENTS 0000373 1/1979 European Pat. Off. .
1184709 2/1959 France .

Primary Examiner—Richard L. Raymond
Assistant Examiner—Raymond Covington
Attorney, Agent, or Firm—Curtis, Morris & Safford

[57] ABSTRACT

The invention relates to imidazole-5-carboxylic acid derivatives in which the imidazole ring is substituted in the 1-position by a 2,6-dialkylphenyl radical and which have the formula

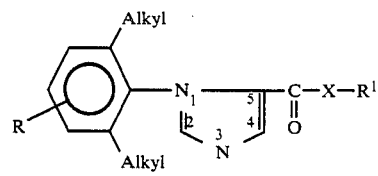

in which
X=O, S or N.

The compounds are obtained from appropriately substituted bisformyl esters, either by reacting the latter with formamide or with ammonium acetate or by subjecting aminomethylene compounds prepared from the bisformyl esters to an intramolecular condensation reaction.

The new substances can be used as biocides, in particular herbicides, fungicides and growth regulators.

12 Claims, No Drawings

1-SUBSTITUTED IMIDAZOLE-5-CARBOXYLIC ACID DERIVATIVES, THEIR PREPARATION AND THEIR USE AS BIOCIDES

This application is a continuation of application Ser. No. 547,937, filed Nov. 2, 1983, now abandoned.

It is known that 1-benzhydryllimidazole-5-carboxylic acid derivatives possess fungicidal and also herbicidal activity (German Offenlegungsschrift No. 2,732,531).

It has now been found, surprisingly, that imidazole-5-carboxylic acid derivatives in which the 1-position of the imidazole ring is substituted by a 2,6-dialkylphenyl radical, i.e. derivatives of 1-(2,6-dialkylphenyl)-imidazole-5-carboxylic acid, which, moreover, can be prepared more easily than the above 1-benzhydryl compounds, are also very good fungicides and also display remarkable herbicidal and growth-regulating properties, and that it is furthermore possible to obtain 1-substituted imidazole-5-carboxylic acid derivatives in a simpler manner than that hiterto described.

The present invention therefore relates to 1-substituted imidazole-5-carboxylic acid derivatives of the formula (I)

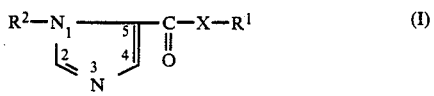

in which
X is O, S or N, particularly O,
$R^1$ denotes hydrogen, phenyl, $C_2$- to $C_6$-alkenyl, preferably $C_3$-alkenyl, or $C_1$- to $C_{12}$-alkyl, in particular $C_1$- to $C_6$-alkyl, it being possible for the alkyl group to be monosubstituted to trisubstituted—also with different substituents—preferably monosubstituted, by $C_1$- to $C_6$-alkoxy, in particular $C_1$- or $C_2$-alkoxy or $C_1$- to $C_3$-dialkylamino or by halogen, and two identical or different radicals $R^1$ being attached to N if X=N. If X=O or S, $R^1$ can also represent the cation of a metal of the I, II or VII group of the periodic system, for instance Zn, Cu or Mn, preferably an alkali metal cation, or ammonium. $R^2$ denotes a radical of the formula (II)

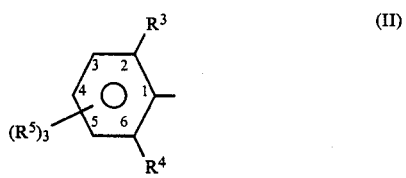

in which
$R^3$ and $R^4$ independently of one another represent a $C_1$- to $C_4$-alkyl group and
the $R^5$s are identical or different radicals belonging to the group comprising hydrogen, $C_1$- to $C_4$-alkyl, $C_1$- to $C_4$-alkoxy and halogen, preferably hydrogen and alkyl, but particularly hydrogen.

The following may be mentioned as preferred radicals $R^2$: 2,6-dimethylphenyl, 2-methyl-6-ethylphenyl, 2,4,6-trimethylphenyl, 3-chloro-2,6-dimethylphenyl, 2,6-diisopropylphenyl and 2,6-diethylphenyl.

The invention also relates to processes for the preparation of the new compounds and to their use as biocides, in particular fungicides, herbicides and growth regulators.

The starting materials for the synthesis of the compounds, according to the invention, of the formula I in which $R^2$ has the meaning indicated above and also those in which $R^2$ additionally represents an alkyl group having 1 to 12, preferably 1 to 6, carbon atoms or a radical of the formulae III or IV

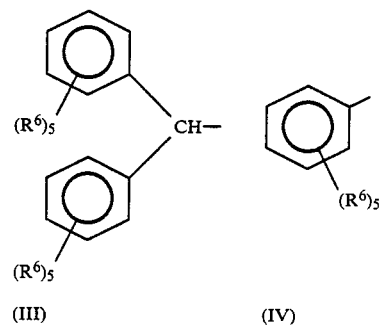

in which the $R^6$s are identical or different radicals denoting hydrogen, halogen, $C_1$- to $C_4$-alkoxy or $C_1$- to $C_4$-alkyl, are bisformyl esters or the enol form thereof of the formulae (V) or (Va), respectively

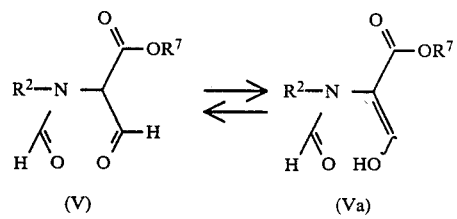

in which $R^2$ represents the radicals mentioned above and $R^7$ represents one of the radicals $R^1$ defined above, preferably methyl or ethyl and especially ethyl, but not H, a metal or ammonium. These esters can be prepared readily by known processes from the corresponding amines by N-alkylating the latter with halogenoacetic acid esters in the presence of organic or inorganic bases, then N-formylating the products with formic acid and then carrying out a C-formylation with formic acid esters in the presence of strong bases such as sodium hydride or alkali metal alcoholates.

In addition to the known process, which, however, is tedious, three process variants are available for the preparation of the 1-substituted imidazole-5-carboxylic acid derivatives from the bisformyl esters:

In process variant (a) the bisformyl esters (V) or (Va) are reacted wit a carboxamide having 1 to 3 carbon atoms, most suitably formamide, which acts at the same time as the solvent, advantageously in the presence of strong acids, preferably using molar quantities of strong mineral acids, such as concentrarted hydrochloric acid, at temperatures of 50 to 250, preferably 120° to 170° C., to give the imidazoles. The progress of the reaction can be followed easily by means of chromatography.

In variant (b) the compounds of the structure (V) or (Va) are reacted with a 5-fold to 30-fold, advantageously 10-fold to 20-fold, molar excess of ammonium acetate in a 5 to 50-fold, especially 20 to 40-fold, molar amount of glacial acetic acid at temperatures of 50° to 180° C., particularly advantageously at the boiling point of the reaction mixture.

In process (c) the aminomethylene compounds VI

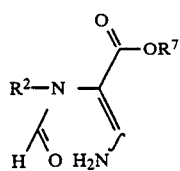

which can be prepared readily by known processes from the compounds (V) or (Va) by reaction with ammonia or ammonium salts are subjected—generally without the necessity for them to be isolated, to an intramolecular condensation reaction which is carried out at such a temperature that the product is removed by distillation at the same time. It is particularly advantageous to regulate the pressure in the distillation at such a level that distillation can be carried out at a bath temperature of 130° to 250° C.

Since products containing the radical —$OR^7$ (bearing in mind the limitation in respect of $R^7$ indicated above) are formed in all cases, this radical is, if desired, substituted or modified in accordance with generally known methods by other radicals out of those mentioned for X and $R^1$, for example by saponification, transesterification amidation. Finally, if apropriate, the possibility of forming a salt or complex salt of, or quaternizing, the imidazole ring, which has a basic reaction, can also be exploited by reacting the product in a known manner with organic or inorganic acids, with metals of the groups Ib, IIb, Ivb or VIII of the periodic system, for example Cu, Zn or Sn, or with alkyl or phenacyl halides.

In general, the desired compounds are obtained in very high purity and in good yields by the procedure according to the invention. This was surprising and could not have been forseen. It would, on the contrary, have been expected that the ester grouping —$OR^7$, which is chemically relatively labile, would be destroyed by saponification or by amide formation, even before the cyclization reaction, under the conditions of the reaction, such as, for example, heating to relatively high temperatures with molar amounts of concentrated hydrochloric acid in formamide.

Compared with the known method for the preparation of 1-substituted imidazole-5-carboxylic acid derivatives, in which the bisformyl compounds are cyclized to give the 2-mercapto compound by means of potassium thiocyanate with elimination of the N-formyl group, and the mercapto group is then removed by oxidation in a second reaction stage [R. G. Jones, J. Am. Chem. Soc. 71 (1949), 644], the procedure claimed constitutes a considerable improvement, since a single-stage reaction takes the place of the two-stage reaction, the elimination of two auxiliary groups, which is unsatisfactory from an economic point of view, is avoided and, last but not least, the inevitable formation of undesirable by-products does not take place.

As already mentioned, the new 1-substituted imidazole-5-carboxylic acid derivatives can be used as biocides. They are distinguished by an excellent fungicidal action. Fungoid pathogens which have already penetrated into the plant tissue can be successfully combated in a curative manner. This is particularly important and advantageous in the case of fungal diseases which can no longer be combated effectively using the otherwise customary fungicides after infestation has taken place. The spectrum of action of the new compounds embraces a large number of different phytopathogenic fungi, such as, for example, *Piricularia oryzae, Plasmopara viticola*, various species of rust and above all *Venturia inaequalis, Cerospora beticola* and powdery mildew fungi, in the cultivation of fruit, vegetables, cereals and ornamental plants.

The compounds are also suitable for use in technical fields, for example in wood preservatives, as preservatives in paints and in coolant-lubricants for metal working or as preservatives in drilling and cutting oils.

The agents can be used as wettable powders, emulsifiable concentrates, sprayable solutions, dusting agents, dressing agents, dispersions, granules or microgranules, in the customary formulations.

Wettable powders are preparations which can be uniformly dispersed in water and which, as well the active compound, also contain, in addition, if appropriate, to a diluent or inert substance, wetting agents, for example polyoxethylated alkylphenols, polyoxethylated fatty alcohols, alkylsulfonates or alkylphenylsulfonates, and dispersing agents, for example sodium ligninsulfonate, sodium 2,2'-dinaphthylmethane-6,6'-disulfonate, sodium dibutylnapthalenesulfonate or the sodium salt of oleylmethyltauride. They are prepared in a customary manner, for example by grinding and mixing the components.

Emulsifiable concentrates can be prepared, for example, by dissolving the active compound in an inert organic solvent, for example butanol, cyclohexanone, dimethylformamide, xylene or higher-boiling aromatic compounds or hydrocarbons, with the addition of one or more emulsifiers. In the case of liquid active compounds, the quota of solvent can also be completely or partially omitted. The following are examples of emulsifiers which can be used: calcium alkylarylsulfonates, such as Ca dodecylbenzenesulfonate, or nonionic emulsifiers, such as fatty acid esters of polyglycols, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, fatty acid esters of sorbitan, fatty acid esters of polyoxyethylenesorbitan or esters of polyoxethylenesorbitol.

Dusting agents can be obtained by grinding the active compound with finely divided solid substances, for example talc, natural clays, such as kaolin, bentonite or pyrophillite, or diatomaceous earth.

Granules can be prepared either by atomizing the active compound onto an adsorptive granulated inert material or by applying concentrations of active compound by means of binders, for example polyvinyl alcohol, sodium polyacrylate or mineral oils, to the surface of carriers, such as sand, kaolinite or a granulated inert material. Suitable active compounds can also be granulated in the manner customary for the preparation of fertilizer granules, if desired as a mixture with fertilizers.

The concentration of active compound is wettable powders is, for example, about 10 to 90% by weight; the remainder up to 100% by weight is composed of customary formulation ingredients. In the case of emulsifiable concentrates the concentration of active compound can be about 10 to 80% by weight. Formulations in the form of dusts contain in most cases 5 to 20% by weight of active compound, while sprayable solutions contain about 2 to 20% by weight. In the case of granules, the content of active compound depends in some cases on whether the active compound is in a liquid or solid form and on the granulating auxiliaries, fillers and the like which are used.

In addition, the active compound formulations mentioned can contain the adhesives, wetting agents, dispersing agents, emulsifiers, penetration agents, solvents, fillers or carriers which are customary in a particular case.

For application, the concentrates present in a commercially available form are optionally diluted in a customary manner, for example in the case of wettable powders, emulsifiable concentrates, dispersions and, in some cases, also microgranules, by means of water. Formulations in the form of dusts and granulated formulations and also sprayable solutions are usually not diluted further with additional inert substances before use.

Mixtures of mixed formulations containing other active compounds, such as, for example, insecticides, acaricides, herbicides, fertilizers, growth regulators or fungicides, are also possible if appropriate. Particularly in the case of mixtures with fungicides, it is also possible in some cases to achieve synergistic increases in activity.

A few examples of formulations may be listed below:

A dusting agent is obtained by mixing 10 parts by weight of active compound and 90 parts by weight of talc or an inert substance and comminuting the mixture in a beaker mill.

A wettable powder which an be dispersed readily in water is obtained by mixing 25 parts by weight of active compound, 64 parts by weight of kaolin-containing quartz as an inert material, 10 parts by weight of potassium ligninsulfonate and 1 part by weight of sodium salt of oleylmethyltauride as a wetting and dispersing agent, and grinding the mixture in a pin mill.

A dispersion concentrate which can be readily dispersed in water is obtained by mixing 20 parts by weight of active compound with 6 parts by weight of an alkylphenol polyglycol ether (Triton X 207), 3 parts by weight of isotridecanol polyglycol ether (8 EO) and 71 parts by weight of a paraffinic mineral oil (boiling range, for example, approx. 255° to 377°C.), and grinding the mixture to a fineness less than 5 microns in an atrrition ball mill.

An emulsifiable concentrate is obtained from 15 parts by weight of active compound, 75 parts by weight of cyclohexanone as solvent and 10 parts by weight of oxethylated nonylphenol (10 EO) as emulsifier.

Surprisingly, however, the compounds according to the invention also possess an excellent herbicidal action in the pre-emergence and post-emergence techniques against annual and perennial weeds. Depending on the dose, this results in inhibition of plant growth or complete destruction of the plants.

The species which can be combated include economically important grass-like weeds, such as Setaria (foxtail), Digitaria (fingergrass), Echinochloa (cockspurgrass), Alopecurus (slender foxtail), Avena (wild oats), Cyperaceae (cyperaceae) and Agropyron (couchgrass) and Sorghum (sorghum). In addition, dicotyledonous weeds of economic importance, such as Matricaria (chamomile), Chrysanthemum (chrysanthemum), Amaranthus (amaranth), Galium (cleavers), Abutilon (China jute) and Sida, are also controlled. In addition, at herbicidally effective application rates the new compounds protect many species of crop plants, so that they can be employed in important major crops, such as, for example, maize, rice, cereals, soya, cotton and rape, for selectively combating undesirable plant growth.

Thus it is possible, for example, to combat effectively by means of the new agents cockspurgrass and amaranth in maize or fingergrass, foxtail, China jute and Sida in soya and cotton crops; but it is also possible to use the new compounds successfully for combating important weeds, such as, for example, cockspurgrass, wild oats, slender foxtail, cyperaceae species and cleavers, in cereal crops and in rice.

Depending on the dosage used, typical growth-regulating effects can also be achieved using the new compounds; thus it is possible, for example, to affect the growth of the plants, and also the constituents of the plants. The compounds are therefore suitable as growth regulators in crops of useful plants, such as, for example, cereals, maize, sugar cane, tobacco, rice and sorghum. On the other hand, it is also possible to control plantations, for instance cultivated lawns, or plant communities on the edges of paths and roads and also ornamental plants.

In this respect the compounds according to the invention can also be advantageously combined with known growth regulators, such as, for example, chloroethylphosphonic acid.

When used as fungicides, the application rate of the compounds according to the invention is generally 0.125 to 1.0 kg/hectare. When used as growth regulators, concentrations between 0.15 and 5.0 kg/hectare, preferably 0.5 to 2.5 kg/hectare, are suitable.

The following examples serve to illustrate the invention further:

PREPARATION EXAMPLES

Example 1 (Example of process variant a)

Ethyl 1-(2,6-diethylphenyl)-imidazole-5-carboxylate 17.8 g (0.06 mole) of ethyl 2-(2,6-diethyl-N-formylanilino)-3-hydroxyacrylate were heated with stirring together with 10 ml of concentrated hydrochloric acid and 50 ml of formamide for 8 hours at an oil bath temperature of 160° C. (internal temperature 140° C.). After cooling, the product was extracted by shaking with a mixture of 100 ml of water and 100 ml of diisopropyl ether, the organic layer was separated off and the aqueous phase was extracted once more with diisopropyl ether. The combined organic phases were dried over sodium sulphate and evaporated. 14.8 g (90% of theory) of the title compound were obtained in the form of a colorless oil of boiling point 145° C./0.01 mm Hg.

$^1$H-NMR (60 MHz, COCl$_3$). $\delta$=1.06 (t, J=7.5 Hz, 6H, Ph—CH$_2$—CH$_3$); 1.14 (t, J=7.5 Hz, 3H, —OCH$_2$—CH$_3$); 2.23 (q, J=7.5 Hz, 4H, Ph—CH$_2$); 4.10 (q, J=7.5 Hz, 2H, —O—CH$_2$—); 7.1-7.3 (m, 3, Ph); 7.50, 7.85 ppm (2s, each 1H, imidazole).

Example 2 (Example of process variant b)

Methyl 1-(2-ethyl-5-methylphenyl)-imidazole-5-carboxylate

A mixture of 15 g (0.06 mole) of methyl 2-(2-ethyl-6-methyl-N-formylanilino)-acrylate, 65 g of ammonium acetate and 100 ml of glacial acetic acid was kept at reflux temperature for 8 hours, a further 50 g of ammonium acetate were then added and the mixture was allowed to react for a further 4 hours under the same conditions. 300 ml of water were then added to the reaction mixture, which was extracted with twice 100 ml of toluene. The organic phase was dried over sodium sulfate, concentrated and chromatographed over silica gel. 9.2 g (67% of colorless tablets of melting point 56° to 57° C. were obtained.

$^1$H-NMR (60 MHz, COCl$_3$). δ=1.05 (t, J=7.5 Hz, 3H, Ph—CH$_2$—CH$_3$); 1.95 (s, 3H, Ph—CH$_3$); 2.25 (q, J=7.5 Hz, 2H, Ph—CH$_2$—); 3.70 (s, 3H, —OCH$_3$); 7.1-7.3 (m, 3H, Ph); 7.50, 7.88 (2s, each 1H, imidazole) ppm.

Example 3 (Example of process variant c)

Ethyl 1-(2,6-diethylphenyl)-imidazle-5-carboxylate 5.5 g (0.019 mole) of the bisformyl compound employed in Example 1 were heated for 1 hour at 65° to 70° C. together with 10 g (0.1 mole) of ammonium carbonate in 100 ml of xylene. During this time ammonium carbonate is evolved by sublimation, and the aminomethylene compound is formed. In order to remove the excess ammonium carbonate completely from the reaction mixture, the temperature is then increased to 120° C. The mixture is allowed to cool, the solvent is removed in vacuo and the residue is heated in a high vacuum (0.01 mm Hg), the desired ethyl 1-(2,6-diethylphenyl)-imidazole-5-carboxylate distilling off from 130° C. Yield 4.3 g (80%).

Examles 4 to 28

The compounds listed in the table below were prepared by the processes described in Examples 1 to 3. Column 3 of the table shows the appropriate process. In the event that the radicals indicated under —X—R$^1$ are other than —OCH$_3$ or —OC$_2$H$_5$, these radicals were introduced in accordance with known processes via the particular acid, which is obtained by saponifying the ester (X—R$^1$=OH).

BIOLOGICAL EXAMPLES

Example 1

Wheat plants in the three-leaf stage are strongly inoculated with conidia of wheat powdery mildew (Erysiphe graminis) and are placed in a greenhouse at 20° C. and a relative humidity of 90 to 95%. 3 days after inoculation, the plants are sprayed until dripping wet with the compounds to be tested in active compound concentrations of 500, 250 and 125 g/liter of spray liquor. After an incubation time of 10 days, the plants are examined for attack by wheat powdery mildew. The degree of attack is expressed in % of leaf area attacked, relative to untreated infested control plants (=100% attack). Table I shows the results.

TABLE I

| Compound according to Example No. | % of leaf area attacked by wheat powdery mildew at ... mg of active compound/liter of spray liquor | | |
|---|---|---|---|
| | 500 | 250 | 125 |
| 9 | 0 | 0 | 0 |
| 15 | 0 | 0 | 0 |
| 16 | 0 | 0 | 0 |
| 17 | 0 | 0 | 0 |
| 18 | 0 | 0 | 0 |
| 23 | 0 | 0 | 0 |
| 25 | 0 | 0 | 0 |
| 26 | 0 | 0 | 0 |
| 27 | 0 | 0 | 0 |
| untreated, infested plants | | 100 | |

Example II

Barley plants in the three-leaf stage are strongly inoculated with conidia of barley powdery mildew (Erysiphe graminis sp. hordei) and are placed in a greenhouse at

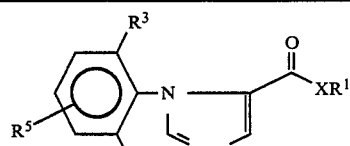

| Example No. | R$^3$ | R$^4$ | R$^5$ | XR$^1$ | Obtained in accordance with Example No. | B.p. (°C.) or m.p. (°C.) |
|---|---|---|---|---|---|---|
| 4 | CH$_3$ | CH$_3$ | H | OH | — | 218–9 |
| 5 | CH$_3$ | CH$_3$ | H | OCH$_3$ | 1 | 89 |
| 6 | CH$_3$ | CH$_3$ | H | OC$_2$H$_5$ | 1 | 54–6 |
| 7 | CH$_3$ | CH$_3$ | H | O(CH$_2$)$_2$—CH$_3$ | — | Oil |
| 8 | CH$_3$ | CH$_3$ | 4-CH$_3$ | OCH$_3$ | 3 | 140/0.1 mm Hg |
| 9 | CH$_3$ | CH$_3$ | 4-CH$_3$ | OC$_2$H$_5$ | 2 | 108–10 |
| 10 | CH$_3$ | C$_2$H$_5$ | H | OH | — | 183–4 |
| 11 | CH$_3$ | C$_2$H$_5$ | H | OCH$_3$ | 3 | 56–7 |
| 12 | CH$_3$ | C$_2$H$_5$ | H | OC$_2$H$_5$ | 1 | Oil |
| 13 | C$_2$H$_5$ | C$_2$H$_5$ | H | OH | — | 203–5 |
| 14 | C$_2$H$_5$ | C$_2$H$_5$ | H | ONa | — | 250 Z |
| 15 | C$_2$H$_5$ | C$_2$H$_5$ | H | OCH$_3$ | 3 | 120/0.1 mm Hg |
| 16 | C$_2$H$_5$ | C$_2$H$_5$ | H | OC$_2$H$_5$ | 2 | 145/0.01 mm Hg |
| 17 | C$_2$H$_5$ | C$_2$H$_5$ | H | O—CH(CH$_3$)$_2$ | — | Oil |
| 18 | C$_2$H$_5$ | C$_2$H$_5$ | H | O—CH$_2$—CH=CH$_2$ | — | Oil |
| 19 | C$_2$H$_5$ | C$_2$H$_5$ | H | O—(CH$_2$)$_7$—CH$_3$ | — | Oil |
| 20 | C$_2$H$_5$ | C$_2$H$_5$ | H | O—CH$_2$—CH$_2$—O—CH$_3$ | — | 53–6 |
| 21 | C$_2$H$_5$ | C$_2$H$_5$ | H | O—CH$_2$—CH$_2$—N(C$_2$H$_5$)$_2$ | — | Oil |
| 22 | i-C$_3$H$_7$ | i-C$_3$H$_7$ | H | OH | — | 232 |
| 23 | i-C$_3$H$_7$ | i-C$_3$H$_7$ | H | OCH$_3$ | 1 | 128–30 |
| 24 | i-C$_3$H$_7$ | i-C$_3$H$_7$ | H | OC$_2$H$_5$ | 3 | 129–30 |
| 25 | i-C$_3$H$_7$ | i-C$_3$H$_7$ | H | O—(CH$_2$)$_2$CH$_3$ | — | Oil |
| 26 | i-C$_3$H$_7$ | i-C$_3$H$_7$ | H | O—CH(CH$_3$)$_2$ | — | 95 |
| 27 | i-C$_3$H$_7$ | i-C$_3$H$_7$ | H | O—(CH$_2$)$_2$—CH(CH$_3$)$_2$ | — | 45–8 |
| 28 | i-C$_3$H$_7$ | i-C$_3$H$_7$ | H | N—(C$_2$H$_5$)$_2$ | — | Oil |

20° C. and a relative humidity of 90 to 95%. 3 days after inoculation, the plants are sprayed until dripping wet with the compounds to be tested in active compound concentrations of 500, 250 and 125 mg/liter of spray liquor. After an incubation time of 10 days, the plants are examined for attack by barley powdery mildew. The degree of attack is expressed as % of leaf area attacked, relative to untreated, infested control plants (=100% attack) The result is shown in Table II.

TABLE II

| Compound according to Example No. | % of leaf area attacked by barley powdery mildew at . . . mg of active compound/liter of spray liquor | | |
|---|---|---|---|
| | 500 | 250 | 125 |
| 9 | 0 | 0 | 0 |
| 15 | 0 | 0 | 0 |
| 16 | 0 | 0 | 0 |
| 17 | 0 | 0 | 0 |
| 18 | 0 | 0 | 0 |
| 23 | 0 | 0 | 0 |
| 25 | 0 | 0 | 0 |
| 26 | 0 | 0 | 0 |
| 27 | 0 | 0 | 0 |
| untreated, infested plants | 100 | | |

Example III

Cucumber plants (variety Delikatess) in the two-leaf stage are inoculated strongly with a conidia suspension of curcubits powdery mildew (Erysiphe cichoracearum). After the spore suspension has dried on for 30 minutes, the plants are placed in a greenhouse at 22° C. and 90% relative humidity. 3 days after infestation, the plants are sprayed until dripping wet with the substances to be tested in the active compound concentrations mentioned in Table III. Assessment is carried out after 10 days. The degree of attack is expressed as % of leaf area attacked, relative to untreated, infested control plants (=100% attack). The result is shown in Table III.

TABLE III

| Compound according to Example No. | % of leaf area attacked by curcubits powdery mildew at . . . mg of active compound/liter of spray liquor | | |
|---|---|---|---|
| | 500 | 250 | 125 |
| 9 | 0 | 0 | 0 |
| 15 | 0 | 0 | 0 |
| 16 | 0 | 0 | 0 |
| 17 | 0 | 0 | 0 |
| 18 | 0 | 0 | 0 |
| 23 | 0 | 0 | 0 |
| 25 | 0 | 0 | 0 |
| 26 | 0 | 0 | 0 |
| 27 | 0 | 0 | 0 |
| untreated, infested plants | 100 | | |

Example IV

Apple stocks of the variety of EM IX in the four-leaf stage are strongly infested with a conidia suspension of apple powdery mildew (Podosphaera leucotricha). The plants are then moved into an air-conditioned chamber at 20° C. and a relative humidity of approx. 100% for 16 hours. They are then placed in a greenhouse at 22° C. and a relative humidity of 85%. 3 days after infestation, the plants are sprayed until dripping wet with the compounds to be tested in the active compound concentrations mentioned in Table IV. The powdery mildew attack is assessed after 2 to 3 weeks, and the degree of attack is expressed as a % of leaf area attacked, relative to untreated, infested control plants (=100% attack). Table IV shows the results.

TABLE IV

| Compound according to Example No. | % of leaf area attacked by apple powdery mildew at . . . mg of active compound/liter of spray liquor | | | |
|---|---|---|---|---|
| | 1000 | 500 | 250 | 125 |
| 12 | 0 | 0 | 0 | 0 |
| 27 | 0 | 0 | 0 | 0 |
| untreated, infested plants | 100 | | | |

Example V

EM IX apple stocks in the four-leaf stage were treated until dripping wet with the compounds to be tested in application concentrations of 500, 250 and 125 mg of active compound/liter of spray liquor. After the coating of active compound had dried on, the plants were strongly infested with conidia of apple scab (Venturia inaequalis), and were placed in a dripping wet state in an air-conditioned chamber having a temperature of 22° C. and a relative humidity of 100%. After an infestation time of 48 hours, the plants were then moved into a greenhouse at 18° C. and a relative humidity of 95 to 100%. They were examined for attack by apple scab (Venturia inaequalis) after an incubation time of 14 days. Assessment was carried out in the customary manner by visual inspection. The degree of attack was expressed as % of leaf area attacked, relative to untreated, infested plants, and is shown in Table V.

TABLE V

| Compound according to Example No. | % scab attack at . . . mg of active compound/liter of spray liquor | | |
|---|---|---|---|
| | 500 | 250 | 125 |
| 15 | 0 | 0 | 0 |
| 16 | 0 | 0 | 0 |
| 18 | 0 | 0 | 0 |
| 23 | 0 | 0 | 0 |
| 25 | 0 | 0 | 0 |
| 26 | 0 | 0 | 0 |
| 27 | 0 | 0 | 0 |
| infested, untreated plants | 100 | | |

Example VI

Wheat plants were treated with the compounds to be tested in application concentrations of 500, 250 and 125 mg of active compound/liter of spray liquor. After the coating of active compound had dried on, the plants were inoculated with spores of wheat brown rust (Puccinia triticina), and were placed in a dripping wet state in an air-conditioned chamber at 20° C. and 100% relative humidity. 24 hours later the plants were brought back into a greenhouse and were examined there 14 days after inoculation for attack by wheat brown rust. The degree of attack was expressed as % of leaf area attacked, relative to untreated, infested control plants (=100% attack). Table VI shows the good action of the new compounds.

TABLE VI

| Compound according to Example No. | % of leaf area attacked by brown rust at . . . mg of active compound/liter of spray liquor | | |
|---|---|---|---|
| | 500 | 250 | 125 |
| 15 | 0 | 0 | 0 |

TABLE VI-continued

| Compound according to Example No. | % of leaf area attacked by brown rust at ... mg of active compound/liter of spray liquor | | |
|---|---|---|---|
| | 500 | 250 | 125 |
| 16 | 0 | 0 | 0 |
| 18 | 0 | 0 | 0 |
| 26 | 0 | 0 | 0 |
| 27 | 0 | 0 | 0 |
| untreated, infested plants | | 100 | |

Example VII

Seeds of weeds and grass-like weeds are sown in sandy loam soil in plastic pots (diameter 9 cm) and are lightly covered with soil. The compounds to be tested, formulated as wettable powders or emulsion concentrates, were sprayed onto the surface of the soil in the form of aqueous suspensions or emulsions. The quantity of water applied per pot was equivalent to 600 liter/hectare. After the treatment, the test pots were placed in a greenhouse and the test plants were cultivated under good conditions for growth (temperature 23° to 25° C.; relative humidity 60 to 80%). After approx. 3 weeks, the plant damage was assessed in accordance with the following rating:

0 = no action
1 = 0 to 20% damage
2 = 20 to 40% damage
3 = 40 to 60% damage
4 = 60 to 80% damage
5 = 80 to 100% damage The assessment numbers of the herbicidal activity of the new compounds are listed in Table VII. The figures show that the substance possess an excellent herbicidal action in the pre-emergence technique against both monocotyledonous and dicotyledonous weeds.

TABLE VII

| Compound according to Example No. | Dose (kg of active substance per hectare) | Herbicidal activity in the pre-emergence technique for | | | |
|---|---|---|---|---|---|
| | | AMR | GAA | SAL | CYI |
| 7 | 2.4 | 5 | 5 | 4 | 5 |
| 9 | 2.4 | 5 | 5 | 3 | 5 |
| 11 | 2.4 | 5 | 5 | 4 | 4 |
| 12 | 2.4 | 5 | 4 | 4 | 5 |
| 15 | 2.4 | 5 | 4 | 5 | 5 |
| 17 | 2.4 | 5 | 5 | 5 | 5 |
| 18 | 2.4 | 5 | 5 | 4 | 5 |
| 20 | 2.4 | 5 | 5 | 5 | 5 |
| 22 | 2.4 | 5 | 2 | 5 | 2 |
| 23 | 2.4 | 5 | 5 | 5 | 5 |

Abbreviations:
AMR = *Amaranthus retroflexus*
GAA = *Galium aparine*
SAL = *Setaria lutescens*
CYI = *Cyperus iria*

Example VIII

Young cereal plants (wheat, barley and rye) in the 3-leaf stage in tray tests in a greenhouse were sprayed until dripping wet with the compounds to be tested in the active compound concentrations (kg/hectare) indicated in Table VIII. The comparison compound employed was 2-chloroethyltrimethylammonium chloride. When the untreated control plants had reached a height of growth of about 55 cm, the growth of all the plants was measured and the inhibition of growth was calculated as a % of the growth of the control plants. Additionally, the phytotoxica action of the compounds was observed. The results are listed in Table VIII. In quoting the inhibition of growth, 100% denotes cessation of growth and 0% denotes growth corresponding to that of the untreated control plants.

TABLE VIII

| Compound according to Example No. | Concentration applied (kg/hectare) | % inhibition of growth for | | | Phytotoxic action |
|---|---|---|---|---|---|
| | | Wheat | Barley | Rye | |
| 17 | 5.00 | 24 | 36 | 31 | no |
| | 2.50 | 18 | 39 | 27 | damage |
| 13 | 5.00 | 25 | 41 | 29 | no |
| | 2.50 | 21 | 39 | 29 | damage |
| 7 | 5.00 | 27 | 35 | 31 | no |
| | 2.50 | 26 | 30 | 32 | damage |
| Comparison[1] | 2.50 | 27 | 8 | 10 | no |
| | 1.25 | 23 | 0 | 0 | damage |

[1] (2-Chloroethyl)-trimethylammonium chloride

Example IX

Inhibition of growth in water rice

Rice plants were cultivated in small plot (2 m × 2 m) and were treated with the compounds indicated during the stage of maximum tillering. The substance can either be applied by spraying or put into the water.

3 weeks after treatment, the growth of all the plants were measured and the inhibition of growth was calculated as a % of the growth of the control plants. Notice was also taken of possible phytotoxic damage caused by the compounds. The results are listed in Table IX. In quoting the inhibition of growth, 100% denotes cessation of growth and 0% growth corresponding to that of the control.

TABLE IX

| Compound according to Example No. | Concentration applied (kg/hectare) | % inhibition of growth | Phytotoxic action |
|---|---|---|---|
| 10 | 2.5 | 18 | no |
| | 1.25 | 15 | damage |
| | 0.62 | 12 | |
| 13 | 2.5 | 25 | no |
| | 1.25 | 21 | damage |
| | 0.62 | 17 | |
| 17 | 2.5 | 23 | no |
| | 1.25 | 22 | damage |
| | 0.62 | 20 | |

Example X

Mixtures with chloroethylphosphonic acid-synergistic effects.

Young cereal plants (wheat, barley and rye) in the 3-leaf stage in tray tests in a greenhouse were sprayed until dripping wet with the test substances and mixtures indicated.

When the untreated control plants had reached a height of growth of about 55 cm, the growth of all the plants was measured and the inhibition of growth was calculated as a % of the growth of the control plants. The phytotoxic action of the compounds was also observed. The results are listed in Table X. In quoting the inhibition of growth, 100% denotes cessation of growth and 0% denotes growth corresponding to that of the untreated control plants.

TABLE X

| Compound according to Example No. | Concentration applied (g/ha) ab inito | inhibition of growth in (%) for Wheat | Barley | Rye | Phytotoxic action |
| --- | --- | --- | --- | --- | --- |
| Chloroethyl-phosphonic acid (A) | 250 | 0 | 0 | 0 | no damage |
| 7 | 800 | 7 | 5 | 5 | |
| 7 + A | 800 + 250 | 20 | 15 | 15 | |
| 13 | 800 | 5 | 5 | 5 | no |
| 13 + A | 800 + 250 | 18 | 14 | 16 | damage |
| 17 | 800 | 9 | 4 | 3 | no |
| 17 + A | 800 + 250 | 19 | 14 | 15 | damage |

It can be seen from Table X that the components of the mixture are not effective or only very slightly effective in the concentrations tested. If, however, the substances are applied together, the action is increased very greatly. This unexpected synergism permits a marked reduction in the application rates.

We claim:

1. A 1-substituted imidazole-5-carboxylic acid derivative of the formula (I)

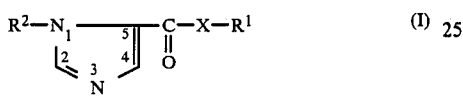

in which
X is O,
$R^1$ is hydrogen, phenyl, $C_2$–$C_6$-alkenyl or $C_1$–$C_{12}$-alkyl, the latter being unsubstituted or substituted by halogen or up to three $C_1$–$C_6$-alkoxy or $C_1$–$C_3$-dialkylamino groups, and if X is N, two identical or different radicals $R^1$ are attached to N, or, if X is O or S, $R^1$ also is a metal cation or ammonium, and $R^2$ is a radical of the formula (II)

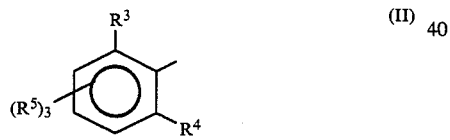

in which
$R^3$ and $R^4$ independently of one another is a $C_1$–$C_4$-alkyl group, and each $R^5$ is identical or different and is a H, $C_1$–$C_4$-alkyl, $C_1$–$C_4$-alkoxy or halogen.

2. A plant-treating composition comprising an effective amount of the compound according to formula I of claim 1 together with an inert carrier.

3. A process for treating plants, which comprises applying an effective amount of the compound according to formula I of claim 1 to the plants or a cultivated area of the plants to be treated.

4. A plant-treating process according to claim 3 for combating harmful fungi, which comprises applying the effective amount to the plants or the cultivated area of the plants to be treated.

5. A plant-treating process according to claim 3 for combating weeds, which comprises applying the effective amount to the plants or the cultivated area of the plants to be treated.

6. A plant-treating process according to claim 3 for regulating the growth of useful plants, which comprises applying the effective amount to the plants or the cultivated area of the plants to be treated.

7. The compound as claimed in claim 1, in which, $R^1$ is hydrogen, $C_1$–$C_6$-alkyl unsubstituted or monosubstituted by $C_1$–$C_6$-alkoxy, $C_1$–$C_6$-dialkylamino or halogen and $R^5$ is hydrogen or alkyl.

8. The compound as claimed in claim 1, in which $R^1$ is hydrogen or $C_1$–$C_6$-alkyl, and $R^5$ is hydrogen.

9. The compound as claimed in claim 1, which is

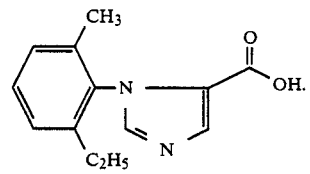

10. The compound as claimed in claim 1, which is

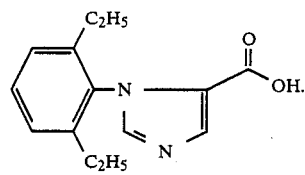

11. The compound as claimed in claim 1, which is

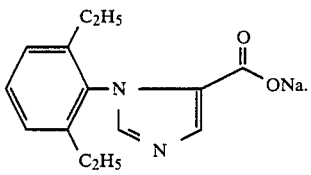

12. The compound as claimed in claim 1, which is

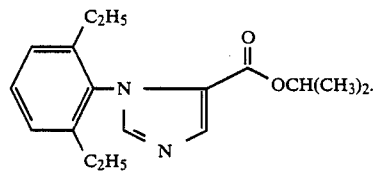

* * * * *